(12) United States Patent
Sender

(10) Patent No.: US 6,606,401 B1
(45) Date of Patent: Aug. 12, 2003

(54) INSPECTION OF EDGE PERIODS OF TWO-DIMENSIONAL PERIODIC STRUCTURES

(75) Inventor: Ben Zion Sender, Modi'in (IL)

(73) Assignees: Tokyo Seimitsu Co. Ltd., Tokyo (JP); Tokyo Seimitsu (Israel) Ltd., Herzlia (IL)

( * ) Notice: Subject to any disclaimer, the term of this patent is extended or adjusted under 35 U.S.C. 154(b) by 0 days.

(21) Appl. No.: 09/257,501

(22) Filed: Feb. 25, 1999

(51) Int. Cl.$^7$ .................................................. G06K 9/00
(52) U.S. Cl. ..................... 382/144; 382/145; 356/237.5
(58) Field of Search ................................. 382/141–151; 348/87, 86, 126, 127, 125, 88, 92; 324/500, 537, 765; 250/310, 559.01, 559.04; 356/237, 237.1, 237.2, 237.5, 388, 394

(56) References Cited

U.S. PATENT DOCUMENTS

| | | | |
|---|---|---|---|
| 5,502,306 A | * | 3/1996 | Meisburger et al. ........ 250/310 |
| 5,917,588 A | * | 6/1999 | Addiego .................. 356/237.2 |

* cited by examiner

Primary Examiner—Samir Ahmed
Assistant Examiner—Vikkram Bali
(74) Attorney, Agent, or Firm—Mark M. Friedman

(57) ABSTRACT

A method for comparing periodic structures, such as wafer dies, by obtaining signals from the images of two swaths of the wafer dies. The signals for each wafer die are then compared to at least the signals from the two nearest neighbor dies. Preferably, these two neighbor dies are located on either side of the die, in the same row as that die. However, for edge dies, at least one neighbor die is located in another row, preferably an adjacent row. Since images are taken from an even number of swaths by the camera in a first row of dies before images are taken from a similar number of swaths in a second row of dies, the camera (and hence the resultant image) is correctly oriented for obtaining signals from the swaths in the second row of dies. This permits the correct comparison of signals obtained from the first swath of the first row of dies to signals obtained from the first swath of the second row of dies. Therefore, the images are correctly aligned, such that the comparison of the signals obtained from an edge die of the first row to the signals obtained from an edge die of the second row is accurate. Thus, the method enables defects at edge dies to be detected with no loss in throughput and with maximal detection sensitivity.

6 Claims, 5 Drawing Sheets

This rectangle represents a single

This rectangle represents a "die swath"

△  Random noise
●  True defect
★  True defect
○  Random noise

This rectangle represents a single

This rectangle represents a "die swath"

INSPECTION OF EDGE PERIODS OF TWO-DIMENSIONAL PERIODIC STRUCTURES

FIELD AND BACKGROUND OF THE INVENTION

The present invention is of an inspection method for detecting irregularities (hereafter referred to as defects) in two-dimensional periodic structures such as wafer dies or photomasks, and so forth. The invention permits sequential inspection of these periodic structures in real-time, which includes the examination of periods at the edge of the two-dimensional structure with no loss of throughput.

Periodic structures such as semiconductor wafer dies, memory cells, and photomasks require inspection during manufacture in order to detect the presence of defects as they appear thus reduce production costs. Such inspection cannot be performed entirely manually, since manual inspection would be too intensive and would require many hours of human labor. Instead, inspection is performed automatically, by moving the object containing the structure relative to an optical system for inspecting at least a portion of the object. For the sake of clarity it is convenient to model the system as a camera of limited width obtaining sequential images of a portion of the object, in a process known as "scanning", until the entire desired area is scanned.

Each area of the object which is scanned by a single stroke of the camera is a "swath". For wafer dies, the width of the swath is typically less than the width of the die For wafers, the swath which includes only a single period (single die) of the wafer is defined as a "die swath". A swath covering the same portion of the die for all dies in the wafer is defined as a "virtual swath". A virtual swath features the images of a number of die swaths, preferably substantially all die swaths in the wafer, concatenated into a long string of die swath images taken from substantially the same portion of each die in the wafer.

An example of the three swath types is given in background art FIG. 1A. A wafer 10 features a plurality of dies 12 which are organized into rows 14. Each die 12 is shown with a die swath 16 in substantially the same location for all dies 12. A set of die swaths 16 from each row 14 is a swath 18. All swaths 18 together form a virtual swath.

A classical detection process is based on the analysis of matching signals obtained from a number of periods. The detection of defects is based on a statistical approach, meaning the probability that a defect will exist on the same location within adjacent dies is very low. Hence detection is based on locating irregularities through the use of three-die comparison method which is shown in FIG. 1B.

FIG. 1B shows a swath 20 which features five die swaths 22 from five dies, labeled as "A", "B", "C", "D" and "E". The intensity difference for images of each pair of adjacent die swaths 22 is compared to a threshold value, the output of the comparison being a comparison signal 26. When intensity difference exceeds the threshold value, comparison signal 26 is said to be significant. Therefore, the proper threshold must be set, such that the system is sensitive enough to detect low contrast defects and robust enough to ignore high contrast noise. Hence, threshold values should represent a tight estimator of pixel noise.

In FIG. 1B, comparison signals 26 are labeled as AB, BC, CD and DE. Each comparison signal 26 is an image marking the position of irregularities where there is a significant deviation between the signals obtained for each pair of adjacent die swaths 22. Various algorithms have been proposed for filtering the signals and for determining the proper threshold at which a different signal from one die indicates a potential defect in the die. Examples of such algorithms are disclosed in U.S. Pat. No. 5,537,669.

A defect image 28 is the result of the defect identification procedure performed with a pair of adjacent comparison signals 26. A defect identification procedure marks a defect in a certain die if irregularities appear at the same location in the comparison with its neighboring dies.

Since defects are expected to be both statistically random and relatively infrequent events, any defect is statistically unlikely to appear in the same location on two or three wafer dies. Thus, by performing a defect identification procedure between comparison signals obtained from adjacent dies, the presence of a defect 25 (if any) can be detected and the detection of random noise is reduced.

The term "random noise" refers to noise that is introduced in the intensity comparison procedure. Such comparison typically has an increased variance, thus there is a finite probability that the intensity comparison will exceed the threshold value to produce random noise 24 when a defect is absent. At typical threshold values the probability of such event is small for one comparison and is almost zero for two such events on the same pixel. Hence the defect identification operation should reduce the occurrence of such events to zero or near-zero levels.

A defect in the die labeled as "B" yields a significant comparison signal 26 between die swaths 22 labeled as "A" and "B" as well as between the dies labeled as "B" and "C", such that the defect identification operation is true at the position of the defect.

The advantage of this method is that the defect identification operation results in the cancellation of much of the noise since a defect should produce significant comparison signals 26 for two adjacent die swaths 22. In addition, such a process is particularly suitable for a real-time image processing system, since the steps required for image acquisition and processing are well defined and are performed repetitively. These steps are as follows. First, an image of a die swath for die "A", or "die swath A", is grabbed and stored in the system memory. Next, an image of a die swath for die "B", or "die swath B", is grabbed and stored. Each image is grabbed as a plurality of frames, which are processing units within a die swath. Each incoming frame of die swath B is aligned to the corresponding frame of die swath A for comparison, such that a reliable comparison signal is obtained.

As all of the images for die swath B are grabbed, a comparison image is produced which is termed image AB. Next, images for die swath C are grabbed and comparison image BC is generated. The defect identification operation which is performed between images AB and BC permits the defects found in die B to be detected. Unfortunately, this method is not effective for detecting defects at edge dies such as dies A and E. For example, defects at die A may be detected as the result of the defect identification operation between AB and BC. Such defects produce a significant comparison signal at AB while the corresponding portion of the BC signal is free of such irregularities. Hence, the defect identification operation for an edge die, such as die A, is performed only once and is sensitive to the presence of high contrast noise, the thereby giving a misleading result.

Thus, the inspection of edge dies has two difficulties. First, such detection requires additional processing steps, for example in order to perform an additional defect identification operation, which are not included in the typical processing path for the remainder of the wafer, reducing system throughput. In addition, this operation produces a significant number of false positive results for the detection of defects because of the presence of random noise.

These problems of the detection of defects at edge dies are known in the art, and have a number of currently known but deficient solutions. The first solution is simply to ignore all edge dies during the inspection process, declaring all such dies to be unfit. This solution is clearly disadvantageous, since eliminating all edge dies is inefficient and costly. The second solution is to increase the comparison threshold such that significant differences need to be even greater for edge dies. This solution eliminates most of the random noise, but also reduces the detection sensitivity. The third solution is to confirm the presence of defects on edge dies using an additional post-processing phase, in which edge dies are examined with a second comparison with a die which is separated from the edge die by two dies. The disadvantage of such method is the additional time overhead required for such an operation.

Yet another solution is to compare signals of images obtained from two swaths of wafer dies, as shown in FIG. 1C. For this solution, at least two rows of wafer dies 14 are required. A comparison is performed between the signals which are obtained from the images of the first die 12 of each row 14, both of which are edge dies 12, effectively giving each edge die 12 two "neighbors" for comparison. However, the compared images have opposite orientations at the edges, such that the orientation of one of the images must be reversed before the comparison can be performed. One disadvantage of this method is that the images from two neighboring swaths 16 are taken at reverse orientations of wafer 10 relative to the camera, often introducing an artifactual deviation in the comparison signals. Such noise sources cause detection sensitivity to be lost in order to avoid false positives for the detection of defects. Thus, a preferred solution would feature the comparison of two or more signals obtained with the same image orientation. Unfortunately, such a solution is not available.

There is thus a need for, and it would be useful to have, a method for detecting defects in a periodic structure, such as a wafer of semiconductor dies, which enables the real-time inspection of edge dies with maximal detection sensitivity and throughput.

SUMMARY OF THE INVENTION

The present invention is of a method for comparing periodic structures, such as wafer dies, by obtaining signals from the images of an even number of virtual swaths of wafer dies simultaneously. The signals for each wafer die are then compared to at least the signals from two other dies. Preferably, these two dies are located on either side of the die, in the same row as that die. However, for edge dies, at least one neighbor die is located in another row, preferably an adjacent row and on the opposite side of the swath.

In the method of the present invention, images are grabbed and processed from an even number of swaths, such as two or more swaths, in the first row of dies before images are taken from equivalent swaths in a second row of dies. The camera (and hence the resultant image) is correctly oriented for obtaining high quality signals from the equivalent swaths in the second row of dies. Such a method permits the correct comparison of signals obtained from swaths of the first row of dies and second row of dies, including edge dies.

Hereinafter, the term "swath" refers to each area of an object, which is scanned by a single stroke of the camera across the object. Hereinafter, the term "periodic structure" includes but is not limited to semiconductor wafer dies, memory cells, and photomasks. The terms "wafer die" and "semiconductor wafer die" refer to a wafer which is divided into dies for the manufacture of semiconductor chips, such that each die becomes an individual chip, such as a memory chip or a microprocessor chip for example. The type of chip produced from each die is not relevant to the method of the present invention.

BRIEF DESCRIPTION OF THE DRAWINGS

The foregoing and other objects, aspects and advantages will be better understood from the following detailed description of a preferred embodiment of the invention with reference to the drawings, wherein.

DETAILED DESCRIPTION OF THE INVENTION

The present invention is of a method for comparing periodic structures, such as wafer dies, at real-time, by obtaining signals from the images of an even number of virtual swaths of the wafer dies. The signals for each die swath of the wafer die are then compared to at least the signals from other two dies. Preferably, these two neighbor dies are located on either side of the die, in the same row as that die. However, for edge dies, at least one neighbor die is preferably located in another row, preferably an adjacent row.

According to the method of the present invention, images are taken from an even number of swaths in a first row of dies before equivalent images are taken from the same number of swaths in a second row of dies, such that the swaths of the dies of the second row are in the same orientation as their corresponding swaths in the first row. The correct alignment between the die images of the same orientation permits a more sensitive comparison of signals obtained from swaths of the first row of dies to signals obtained from swaths of the second row of dies.

The method of the present invention has a number of advantages over methods which are known in the art. First, the method of the present invention permits edge dies to be inspected, unlike certain methods known in the art which simply ignore the edge dies during the inspection procedure, forcing these edge dies to be discarded. Clearly, discarding the edge dies is wasteful and inefficient.

Second, the method of the present invention permits the comparison of signals obtained from images of edge dies, which are already in the correct orientation. Thus, there is no comparison between die swaths acquired using reverse stage and camera polarity, which may introduce noise related to the signal detection system.

Third, the method of the present invention supports multi-die comparison for more than three dies. Since a virtual swath is scanned according to a preferred embodiment of the method according to the present invention, the same die swath is scanned over the whole wafer. Therefore, each virtual swath contains a large population of periods, which permits more advanced statistical analysis of a larger ensemble of dies for the determination of threshold values.

In the example of the present invention which is given below, the period is assumed to be a single die, and the images are assumed to be obtained from a wafer of dies, it being understood that this is for the purposes of description only and is not meant to be limiting in any way.

The principles and operation of a method for inspecting edge dies, or any other period of a periodic structure which lacks at least one neighbor along the scanning axis according to the present invention, may be better understood with reference to the drawings and the accompanying description, it being understood that these drawings are given for illustrative purposes only and are not meant to be limiting.

Figure 1A:
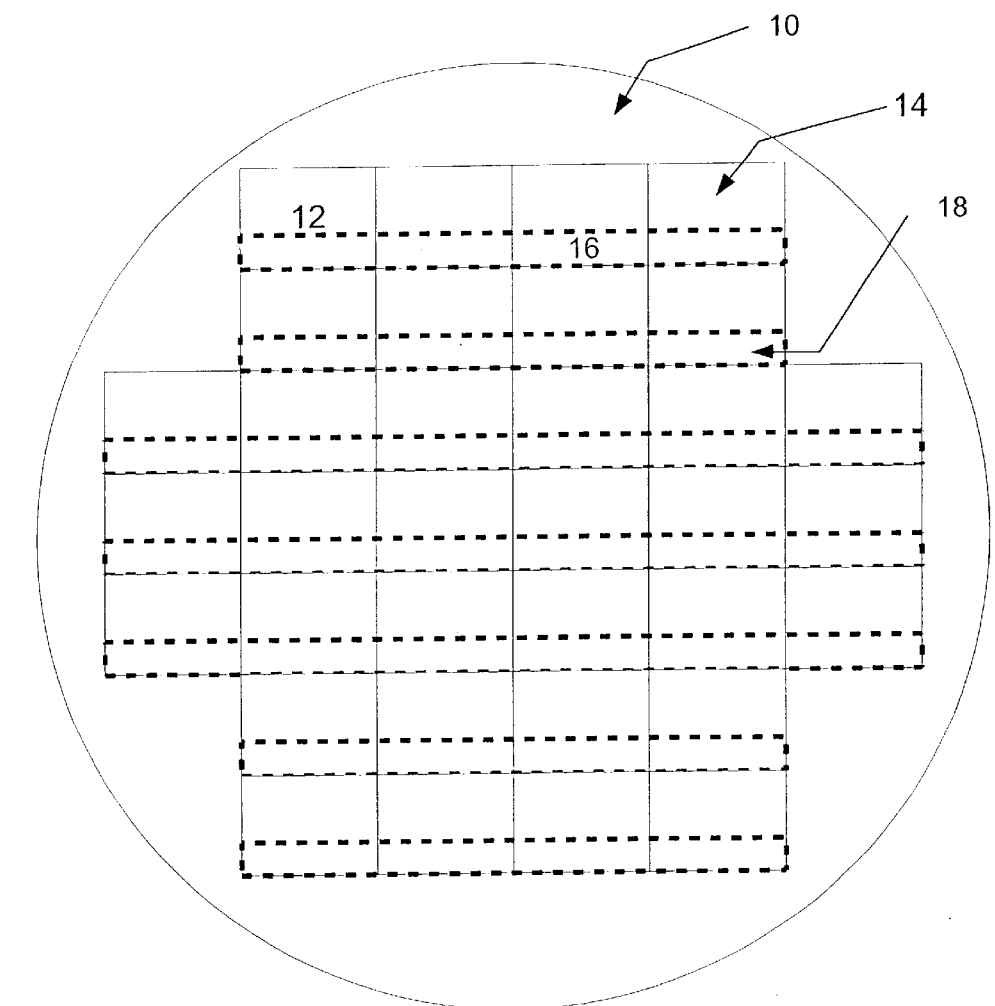
FIGS. 1A–1C illustrate background art features of defect inspection for wafer dies.
Figure 1A:
Figure 1A:
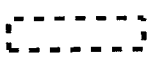
Figure 1B:
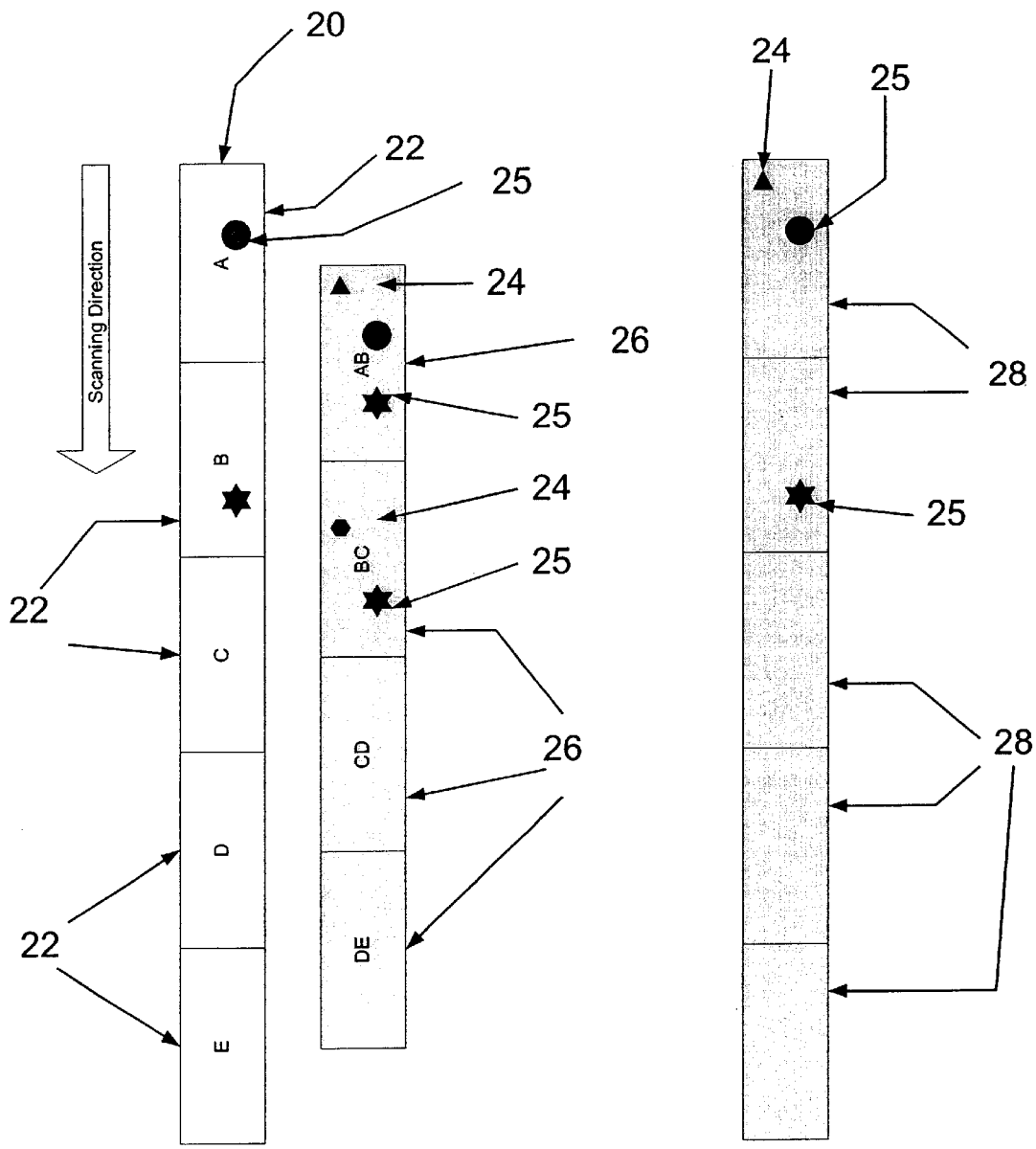
Figure 1C:
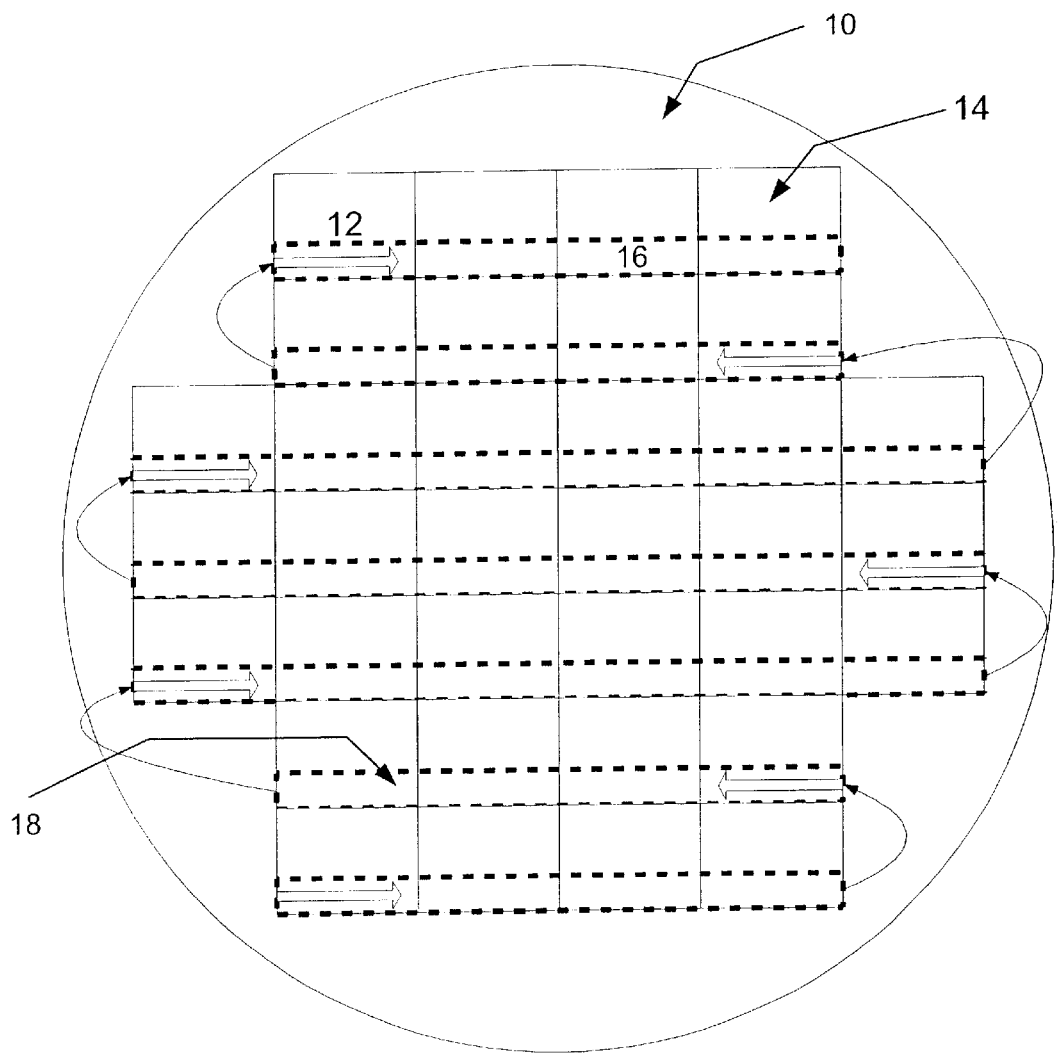
Figure 1C:
Figure 1C:
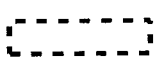
Figure 2:
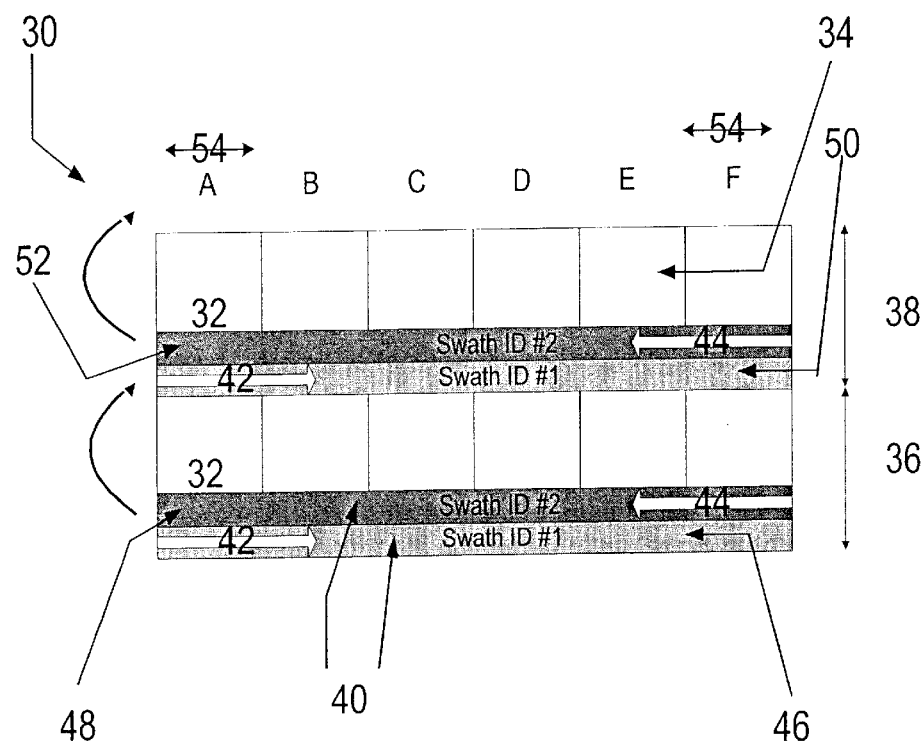
FIG. 2 is a schematic block diagram of an exemplary plurality of wafer dies being examined according to the method of the present invention.

Referring now to the drawings, FIG. 2 is a schematic block diagram of a plurality of wafer dies being examined according to the method of the present invention. FIG. 2 shows a portion of a wafer 30, containing a plurality of dies 32. Dies 32 are organized into two rows 34, each row 34 containing six dies 32. It should be noted that the number of dies 32 and rows 34 is given only for the purposes of description and is not intended to be limiting in any way, since each row 34 needs to contain at least one die 32. Wafer 30 should contain at least two rows 34, including a first row 36 and a second row 38 as shown.

The paths of two virtual swaths 40 are indicated in FIG. 2 as arrows, with a first swath 42 (labeled as "swath ID #1") and a second swath 44 (labeled as "swath ID #2"). Each virtual swath 40 is an image obtained by a single scanning stroke of the stage or camera over substantially the entirety of wafer 30. Each virtual swath 40 includes less than the entirety of the width of each die 32, such that at least two such swaths 40 are required to cover the entirety of the width of each die 32. The orientation of first virtual swath 42 is opposite to the orientation of second virtual swath 44, as shown by the direction of the arrows. The camera (not shown) scans a first swath 46 in first row 36, as a portion of first virtual swath 42, and then scans a second swath 48 for first row 36, as a portion of second virtual swath 44. Thus, both first swath 46 and second swath 48 are scanned for first row 36.

Next, both a first swath 50 and a second swath 52 are scanned for second row 38, as a portion of first virtual swath 42 and second virtual swath 44, respectively. The orientation of the images of first swath 46 for first row 36 and first swath 50 for second row 38 is therefore substantially identical. Similarly, the orientation of the images of second swath 48 for first row 36 and second swath 52 for second row 38 is also substantially identical.

Both edge dies 54 (columns labeled as "A" and "F") of first row 36 and second row 38 have only a single neighbor within the same row.

Figure 3:
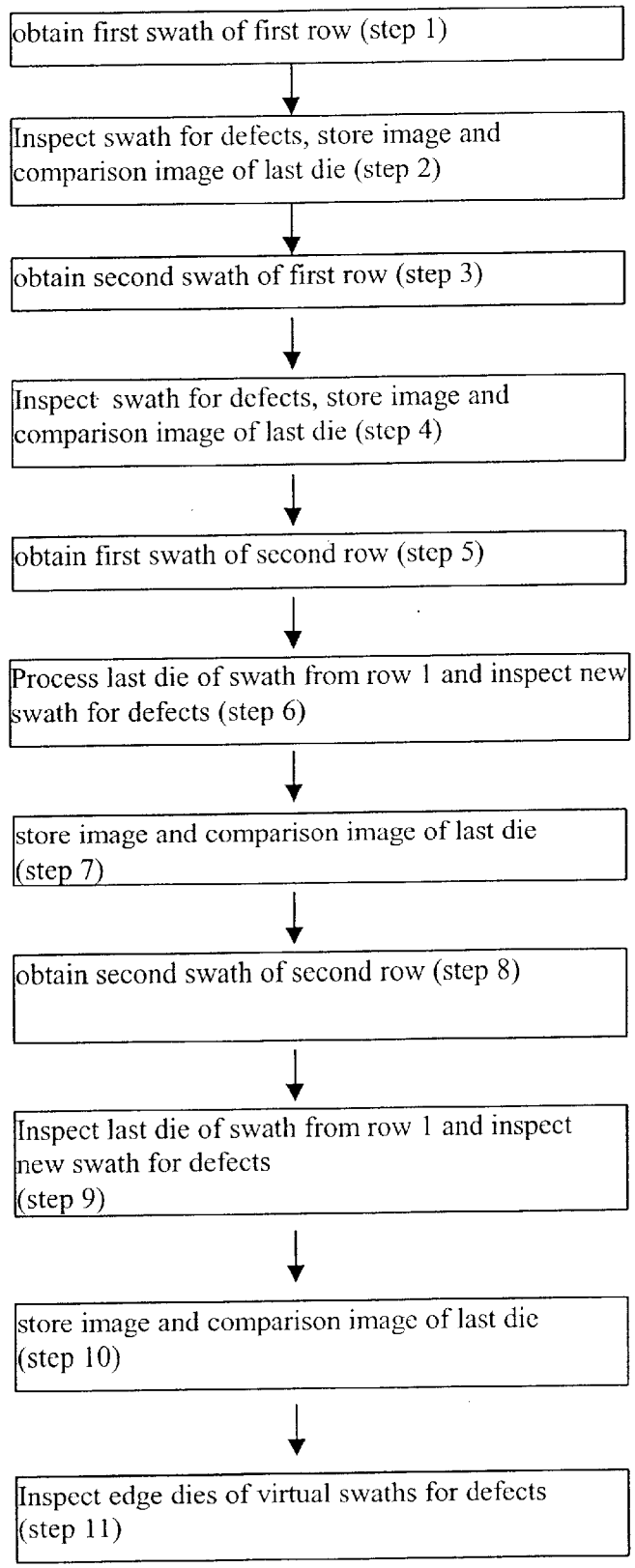
FIG. 3 is a flowchart of the method of the present invention.

FIG. 3 shows a flowchart of the method of the present invention for inspecting a wafer of dies for defects, the wafer having at least a first row of dies and a second row of dies. For both the first and second row of dies, there are two edge dies. The steps of the method are as follows.

In step 1, a camera obtains an image of a first swath of the first row of wafer dies. The width of the first swath is less than the width of a die, such that at least two swaths are required to cover the entire width of the dies. In step 2, at the end of the process of scanning the swath and inspecting it for the presence of defects, the system stores both the image, described as "F" and the comparison image, described as "EF", of the last die in the swath (die in column F of the first row).

In step 3, the camera obtains an image of a second swath of the first row of wafer dies. The orientation of the first swath is opposite to that of the second swath. In step 4, at the end of the process of scanning the swath, the system stores both the image, described as "A" and the comparison image, described as "BA", of the last die in the swath (the die of the first row in the column labeled as "A")

In step 5, the camera obtains an image of a first swath for the second row of wafer dies. The orientation of the image for the first swath of the first row and the first swath of the second row are substantially identical. In step 6, the swath is inspected for the presence of defects as a continuation of first swath, such that the first swath of the first row and the first swath of the second row are combined into the same virtual swath. For the continuation of the inspection procedure, preferably a defect identification operation is performed with comparison image "FA" (comparison between dice F and A) and the stored comparison image "EF" to detect defects in edge die "F" of the first row. In step 7, at the end of the process of scanning the swath, the system repeats the process of storing the image of the last die, such that the image is available for the processing of subsequent rows.

In step 8, the camera obtains an image of a second swath for the second row of wafer dies. The orientation of the image for the second swath of the first row and the orientation of the second swath of the second row are substantially identical. In step 9, the swath is inspected for the presence of defects as a continuation of first swath, such that the first swath of the first row and the first swath of the second row are combined into the same virtual swath. For the continuation of the inspection procedure, preferably a defect identification operation is performed with comparison image "AF" (comparison between A and F) and the stored comparison image "BA" to detect defects in edge die "A" of the second row. At the end of the inspection of the second swath, in step 10, the system again performs the step of storing of the image of the last die for the processing of subsequent rows.

After an even number of virtual swaths has been inspected, in step 11, the system preferably inspects dies, which are on the borders of the virtual swath for defects. Eventually, each virtual swath has two (border) dies, which have not been previously inspected. However the remainder of the edge dies which reside within the virtual swath are fully inspected under real-time conditions.

In the previous discussion, the method of the present invention was specifically described with regard to wafer dies. More generally, the method of the present invention can be described as a method for the inspection of random defects in periodic structures by comparing two or more periods to one period of the structure, such that each period of the structure is compared to two neighboring periods. For periods of the structure which lie on the edge of the structure, such that the edge period has only one adjacent neighbor in the same row, at least one of the two neighbors is not directly adjacent to the edge period. The method of the present invention accommodates such edge periods by scanning an even number of swaths of opposing orientation for each row of periods, before obtaining the same swaths for the next row of periods. Thus, all sequentially equivalent swaths of each row have the same orientation.

The image of a neighboring period which is not directly adjacent to an edge period, or "non-adjacent period", therefore has the same orientation for the first swath as the image of the edge period itself. Thus, the image of the first swath of the non-adjacent period can be directly compared to the image of the first swath of the edge period in order to perform a neighboring comparison.

As noted previously, examples of such periodic structures for which the method of the present invention is suitable include, but are not limited to, semiconductor wafer dies and photomasks. For wafers, each die is a period, and for photomasks, each hole in the photomasks is a period.

It will be appreciated that the above descriptions are intended only to serve as examples, and that many other embodiments are possible within the spirit and the scope of the present invention.

What is claimed is:

1. A method for inspecting a two-dimensional structure for a presence of a defect, the structure containing a plurality of periods, the structure having at least a first row of periods and a second row of periods, at least one border period of each row being an edge period, the method comprising the steps of:

(a) obtaining images of at least a first swath and a second swath in the first row by a scanning motion along said first swath and said second swath, respectively, such that an even number of swaths is obtained in the first row;

(b) obtaining an image of at least a first swath in the second row corresponding to said first swath of the first row, said first swath of the second row having a substantially identical orientation as said first swath of the first row; and (c) comparing a portion of said image corresponding to the edge period at the end of said first swath of the first row to a portion of said image corresponding to the edge period at the beginning of said first swath of the second row, such that at least a first neighboring comparison is performed for the edge period of the first row for said first swath.

2. The method of claim 1, wherein the first row features an additional period, the method further comprising the steps of:

(d) comparing a portion of said image corresponding to the edge period of said first swath of the first row to a portion of said image corresponding to said additional period of said first swath of the first row, such that a second neighboring comparison is performed for the edge period of the first row for said first swath; and (e) examining said first neighboring comparison and said second neighboring comparison to determine if a defect exists in the edge period of the first row.

3. The method of claim 2, wherein said structure is a wafer of dies, such that each die is a period.

4. The method of claim 2, wherein said structure is a photomask featuring a plurality of holes, such that each hole is a period.

5. A method for inspecting at least a portion of a wafer of dies for a defect, the wafer having at least a first row of dies and a second row of dies, each of the first and second row of dies including at least a first die and a second die, the first die being an edge die for both the fist row of dies and the second row of dies, the steps of the method comprising:

(a) obtaining an image of a first swath of the first row of wafer dies by a scanning motion along said first swath, a width of said first swath being less than a width of the first row;

(b) obtaining an image of at least a second swath of the first row of wafer dies by a scanning motion along said second swath, an orientation of said first swath being opposite to an orientation of said second swath, such that images of an even number of swaths are obtained for the first row;

(c) obtaining an image of a first swath of the second row of wafer dies, said orientation of said image of the first swath of the first row and an orientation of said first swath of the second row being substantially identical;

(d) comparing a portion of said image corresponding to the edge die at the end of said first swath of the first row to a portion of said image corresponding to the preceding die of said first swath of the first row, such that a first neighboring comparison is performed for the edge die of the first row for said first swath; and (e) comparing said portion of said image corresponding to the edge die at the end of said first swath of the first row to a portion of said image corresponding to the edge die at the beginning of said first swath of the second row, such that a second neighboring comparison is performed for the edge die of the first row for said first swath for inspecting the edge die for the defect.

6. The method of claim 5, further comprising the step of:

(f) examining said first neighboring comparison and said second neighboring comparison to determine if a defect exists in the edge die of the first row.

\* \* \* \* \*